United States Patent [19]
Meder

[11] Patent Number: 5,866,419
[45] Date of Patent: Feb. 2, 1999

[54] ROLLER BOTTLE

[76] Inventor: Martin G. Meder, 121 Park Ave., Hightstown, N.J. 08520

[21] Appl. No.: 713,115

[22] Filed: Sep. 16, 1996

[51] Int. Cl.[6] ................ C12N 5/00; C12M 1/24
[52] U.S. Cl. .......... 435/394; 435/288.1; 435/298.2; 435/299.2; 435/304.1; 215/382; 215/DIG. 8
[58] Field of Search ............... 435/298.1, 298.2, 435/299.2, 304.1, 288.1, 394; 215/379, 382, DIG. 8; 366/220, 232, 236; D9/500, 516, 549, 559, 561; D24/224; 220/660, 669

[56] References Cited

U.S. PATENT DOCUMENTS

| | | | |
|---|---|---|---|
| 99,612 | 2/1870 | Wells | 366/220 |
| D. 189,372 | 11/1960 | Adell | D9/561 |
| D. 199,203 | 9/1964 | Dailey | D9/561 |
| D. 253,032 | 10/1979 | White | D9/561 |
| D. 318,800 | 8/1991 | Serkes | D9/396 |
| 1,241,176 | 9/1917 | Watts | 408/229 |
| 3,702,806 | 11/1972 | Oliva | 435/304.1 |
| 3,941,661 | 3/1976 | Noteboom | 195/127 |
| 4,074,778 | 2/1978 | Morrell | 175/91 |
| 4,238,568 | 12/1980 | Lynn | 435/285 |
| 4,283,495 | 8/1981 | Lynn | 435/240 |
| 4,317,886 | 3/1982 | Johnson | 435/285 |
| 4,330,216 | 5/1982 | Johnson | 366/222 |
| 4,337,104 | 6/1982 | Lynn | 156/69 |
| 4,448,879 | 5/1984 | Fabricius | 435/2 |
| 4,517,293 | 5/1985 | Fabricius | 435/68 |
| 4,717,668 | 1/1988 | Keilman | 435/296 |
| 4,749,654 | 6/1988 | Karrer | 435/240.21 |
| 4,761,936 | 8/1988 | Suzuki | 53/510 |
| 4,810,652 | 3/1989 | Witt | 435/296 |
| 4,824,787 | 4/1989 | Serkes | 435/285 |
| 4,829,004 | 5/1989 | Varani | 435/296 |
| 4,912,048 | 3/1990 | Smith | 435/296 |
| 4,912,058 | 3/1990 | Mussi | 435/285 |
| 4,962,033 | 10/1990 | Serkes | 435/240.243 |
| 4,966,853 | 10/1990 | Matsuda | 435/284 |
| 5,010,013 | 4/1991 | Serkes | 435/285 |
| 5,016,688 | 5/1991 | Suzuki | 141/170 |
| 5,084,393 | 1/1992 | Rogalsky | 435/284 |
| 5,151,366 | 9/1992 | Serkes | 435/285 |
| 5,152,592 | 10/1992 | Krayer | 312/238 |
| 5,168,058 | 12/1992 | Bohak | 435/240.23 |
| 5,272,084 | 12/1993 | O'Connell | 435/240.243 |
| 5,330,908 | 7/1994 | Spaulding | 435/240.24 |
| 5,426,037 | 6/1995 | Pannell | 435/70.21 |
| 5,645,190 | 7/1997 | Goldberg | 220/674 |

FOREIGN PATENT DOCUMENTS

| | | | |
|---|---|---|---|
| 912772 | 8/1946 | France | 366/220 |
| 25 36 097 | 3/1977 | Germany | 435/288.1 |

OTHER PUBLICATIONS

Voelcker, H.B., Let's Talk About Size, Tooling and Production, Sep. 1995, pp. 17–20.

M. Gardner, "The Unexpected Hanging", Simon and Schuster, New York, 1969, pp. 212–225.

H. Rademacher et al., "The Enjoyment of Mathematics", Princeton University Press, Princeton, 1957, pp. 163–177.

J. Casey et al., "Reuleaux Design Tutorial", Feb. 14, 1996, on Internet at http://commando.me.berkeley.edu/~willchui/tutorial.html.

Anon., "Magic Geometric Constants", Dec. 30, 1995, on Internet at http://www.mathsoft.com/asolve/constant/magic/magic/html.

*Primary Examiner*—William H. Beisner

[57] ABSTRACT

The invention is a roller bottle having a cross-section that is substantially a non-circular closed curve of constant width, wherein said curve is preferably a Reuleaux triangle or a Reuleaux triangle with rounded corners and the use of the roller bottle for cell culture. This provides several benefits: 1) a larger surface area per unit volume than a circular cross-section, promoting growth of anchorage dependant cells while maintaining an easily harvested and cleaned smooth wall. 2) a translational motion in addition to the usual circular motion, which is expected to enhance gas exchange, especially at the cap, which normally sits on an axis and has low angular velocity. 3) greater agitation of the growth medium inside the bottle, without the need for difficult to manufacture inserts or internal baffles.

3 Claims, 3 Drawing Sheets

ROLLER BOTTLE

FIELD OF THE INVENTION

This invention relates to roller bottles, commonly used in mammalian cell culture.

BACKGROUND OF THE INVENTION

The culture of some zooblast or animal cells, microorganisms, fungi and plant cells is anchorage dependent; the cells need a surface to grow on. One way that this is done is through the use of cylindrical roller bottles as horizontally rotated bioreactors. A liquid nutrient medium inoculated with cells fills the horizontal bottle to a shallow depth (below the bottle opening) and the bottle is rotated by two horizontal drive rollers upon which it rests. Some bottles are provided with protruding drive rings or collars at the perimeter of the top and bottom of the cylinder. Gas exchange, oxygen in and carbon dioxide out for mammalian cells, is generally accomplished at a breather cap on the bottle, which, for example, is provided with a hydrophobic porous membrane and one or more holes at the end of the cap. Alternatively, the gas exchange can be accomplished by diffusion through the walls, augmented by the presence of micropores in the walls. After a time, the cells that have grown on the inside walls are harvested by scraping them off with a blade. Increasing the surface area to volume ratio of the bottle increases the yield of cells from each bottle. In the past this has been accomplished by providing the surface of the bottle with ribs, pleats, ridges, grooves, flutes or corrugations that run either perpendicular or parallel to the axis of the bottle. Despite the introduction of ribbed bottles, smooth wall bottles are still sold. This may be because they are easier to harvest and clean, especially when using automation. Also, reusable bottles such as glass may be impractical to mold with ribs, in comparison to the disposable plastic bottles. Surface area increase is also achieved by using a bioreactor shaped as hollow cylindrical annulus, and by putting packing material or brushes inside the bottle. Agitation of the solution has been increased by the use of inserts and high rotation speeds. The bottles are usually constructed of either glass, stainless steel or a clear plastic, such as polystyrene, polyurethane, polyvinyl chloride, polycarbonate, polyolefins such as polypropylene, polyethylene terephthalate with glycol additives, ethylene glycol-1,4, cyclohexane dimethanol terephthalate copolyester and the like. Transparent materials are preferred, as cell growth can be monitored by placing the bottle on an inverted microscope. Cell adhesion is improved by treatment with silane coupling agents, plasma etching and fibronectin treatment, for example. For repeat use, glass vessels are sometimes siliconized to prevent the surface from becoming rough.

SUMMARY OF THE INVENTION

The invention is a roller bottle having a cross-section that is substantially a non-circular closed curve of constant width, wherein said curve is preferably a Reuleaux triangle or a Reuleaux triangle with rounded corners and the use of the roller bottle for cell culture.

It is an object of this invention to provide a roller bottle with a larger surface area per unit volume than a circular cross-section, promoting growth of anchorage dependant cells while having the option of an easily harvested and cleaned smooth wall.

It is another object of this invention to provide a roller bottle with a translation motion in addition to the usual circular motion, which is expected to enhance gas exchange, especially at the cap.

It is another object of this invention to provide an environmentally beneficial improved roller bottle that promotes reuse rather than disposal because it has an associated mold design that is simple enough to allow being manufactured from glass.

It is another object of this invention to provide an improved roller bottle that is adaptable to automated cell-harvesting and cleaning machinery.

It is another object of this invention to provide an improved roller bottle that has the same width as existing roller bottles, so as to accommodate existing roller culture equipment.

It is yet another object of this invention to provide a roller bottle with greater agitation of the growth medium inside the bottle, via translational motion and fluid impacting the bottle walls, without the need for difficult to manufacture inserts or internal baffles or high rotation speeds.

DETAILED DESCRIPTION OF THE INVENTION

Figure 1:
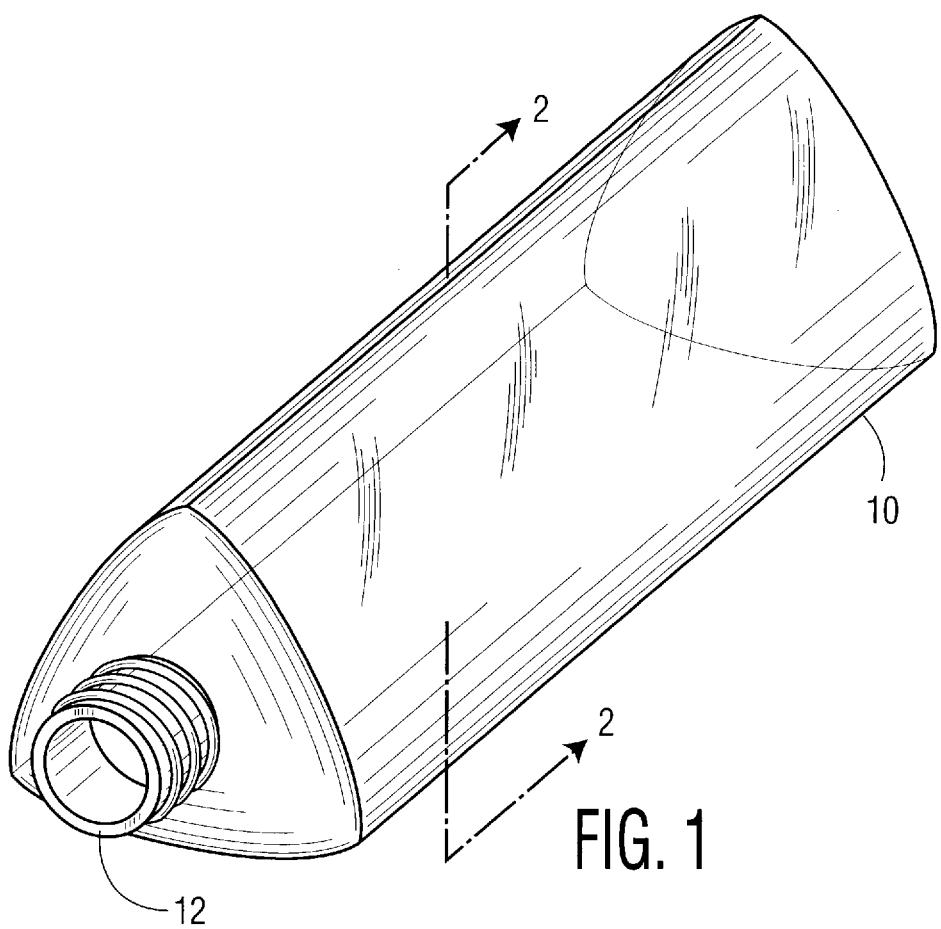
FIG. 1 shows a perspective view of a roller bottle for one embodiment of the invention.

For a curved object to roll smoothly, it should have constant width when measured anywhere across its width. Many believe that the only such curve is a circle, but there are an infinite number of such curves. They are not generally encountered in industry, because most machinery requires that the horizontal axis running perpendicular to the curve remain in a fixed location, which it doesn't for non-circular rollers; they have axes that have a back-and-forth translation motion while rolling. Paradoxically, each non-circular curve of constant width has less cross-sectional area than a circle of the same width, but the same perimeter. The non-circular curve of least cross-sectional area is the Reuleaux triangle. A Reuleaux triangle is mathematically constructed by placing the point of a compass at one corner of an imaginary equilateral triangle and drawing a circular arc from one remaining corner to the other, repeating this for each corner. Detailed discussions of this construction, and construction of other non-circular curves of constant width and related mathematics, can be found in Gardner, M., "The Unexpected Hanging", Simon and Schuster, New York, 1969, pp. 212–255 and Rademacher, H., et al., "The Enjoyment of Mathematics", Princeton University Press, Princeton, 1957, pp. 163–177 and Casey, J., et al.,"Reuleaux Design Tutorial", Feb. 14, 1996 on the Internet at http://commando.me.berkeley.edu/~willchui/tutorial.html and Anon., "Magic Geometric Constants", Dec. 30, 1995, on the Internet at http//:www.mathsoft.com/asolve/constant/magic/magic/html, all incorporated herein by reference as if in they had been set forth in their entirety.

The practical uses of Reuleaux triangle shapes has apparently been limited to square hole drills and as the rotor of the Wankel rotary engine. Square hole drills require special chucks to accommodate the lateral motion of the axis of the drill, lateral axis motion in a rotating device normally being something to be avoided.

A Reuleaux triangle roller bottle of a given width will have less cross-sectional area than a cylindrical bottle of the same width, but the same wall surface area. The wall surface area (excluding the ends) is the same because all curves of the same constant width have the same perimeter (see Rademacher at 177). Hence, it will have a greater surface area to volume ratio and its volume will be less and it would require less nutrient medium to fill it. The cross sectional area for a Reuleaux triangle of width w is $½(\pi-\sqrt{3})w^2$ (see Gardner at 215), while that for a circle is $¼ \pi w^2$. Roller bottles have a long aspect ratio, a width of 110 mm and length of 585 mm being typical, and are filled to a shallow depth, so to a first approximation the ends of the bottle can be ignored. If the bottle lengths are equal, the lengths cancel, and to a first approximation a Reuleaux triangle roller bottle of given width compared to a cylindrical roller of the same width will have a surface area to volume ratio of $¼\pi w^2/½(\pi-\sqrt{3})w^2$ or 1.11 or 11% greater than that of a cylindrical roller bottle.

The largest case translational motion expected would occur when two drive roller surfaces are far enough apart to just barely support a roller bottle. The motion of a cap located at the center of such a bottle can be described by a Reuleaux triangle standing on a corner and comparing it to one rotated 180° so it is standing on an arc. When standing on a corner, the distance to the center of an inscribed equilateral triangle would be $(1-1/\sqrt{3})w$ or about 0.4226w, but when it rolls to the other position (180° away), the center would be 1 minus this value or 0.5774 w. For a 110 mm bottle, this means that the cap would have a best case translational motion of 8.5 mm about the center (at 0.5 w) or 17 mm across the center. A practical roller drive apparatus will have rollers spaced closer than this and so the actual amount of translation will be less than this value and will be a function of the specific equipment used. Of course, in a conventional cylindrical roller bottle, the cap will simply remain at 0.5 was it rolls. This translational motion in addition to the circular motion at the cap provides greater air turbulence and entrainment than the purely circular motion of a cylindrical roller and, hence more rapid gas exchange can be expected when a breather cap is used. The translational motion also assists in agitating the medium inside the bottle, further improving gas exchange.

Figure 2:
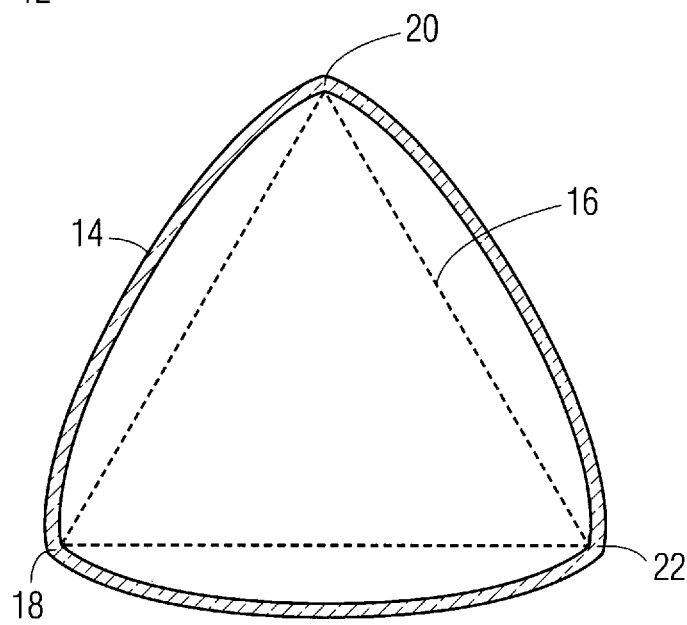
FIG. 2 shows a cross-section of the roller bottle of FIG. 1, said cross-section describing substantially a Reuleaux triangle, in this example.

FIG. 1 shows an embodiment of a Reuleaux triangle roller bottle 10 of this invention, provided with a screw thread finish 12 adapted to receive a cap. However, those skilled in the packaging art will appreciate that a tapered finish adapted to receive a stopper, or other press fit connection, could be used instead. The cross-section of the embodiment of FIG. 1 is shown in FIG. 2 as Reuleaux triangle 14. Here the mathematical construction of a Reuleaux triangle may be seen. An imaginary equilateral triangle 16 is constructed, the length of any leg of this triangle being the desired width. The point of a compass (not shown) is placed at 18 and a circular arc is drawn from opposing corner 20 to 22. The same procedure is repeated by placing the point of a compass at corner 20 and drawing an arc from corner 22 to 18, and again at corner 22 drawing an arc from corner 18 to 20. The connected arcs terminated at corners 18 and 20, 20 and 22 and 20 back to 18 describe a closed curve of constant width known as a Reuleaux triangle which is the cross-section of a bottle of the invention.

Figure 3:
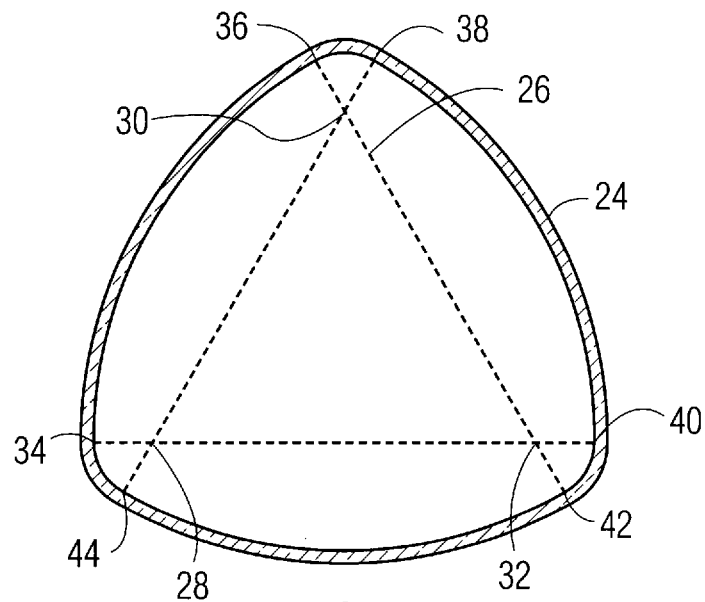
FIG. 3 shows a cross-section of a roller bottle (not shown), that describes substantially a Reuleaux triangle with rounded corners, for another embodiment of the invention.

Referring now to FIG. 3; it may be desirable to avoid sharp inside bottle corners for ease of cleaning the bottle. In this case, some surface area to volume advantage can be sacrificed and a Reuleaux triangle with rounded corners may be used instead, as seen in the bottle (not shown) cross-section 24. This shape may be constructed by extending the legs of an imaginary equilateral triangle 26. Place the point of a compass (not shown) at point 28 and draw an arc from points 34 to 44, with the point of a compass at the same location 28 draw arc connecting points 38 and 40. Repeat this process with compass point at point 30, drawing an arc from point 42 to 44 and then from point 36 to 38. Finally, repeat this process with compass point at point 32, drawing an arc from point 40 to 42 and then from point 34 to 36. The joined arcs terminated at points 34 and 36, 36 and 38, 38 and 40, 40 and 42, 42 and 44 and 44 back to 34 describe a cross-section that is a Reuleaux triangle with rounded corners, having a width equal to one of the extended legs, such as that connecting points 38 and 44.

Higher order roller shapes may be constructed, such as pentagons, heptagons, nonagons, undecagons and the like and may be of value if the existing roller apparatus cannot accommodate too much motion in the bottle cap. They are constructed in a fashion similar to the above, keeping two rules of construction in mind: 1) the roller must have an odd number of sides; and 2) the maximum angle for any arc is 60°. The next highest order is that of a pentagonal non-circular closed curve of constant width. A pentagonal roller bottle (not shown) would have only slight surface area to volume advantage, but there would still be translational cap motion in addition to the circular motion assisting in gas exchange, and there would still be agitation. Note that the pentagonal shape does not have to be regular, that is, have equal length sides, so long as the maximum included angle for any arc doesn't exceed 60°.

Figure 4:
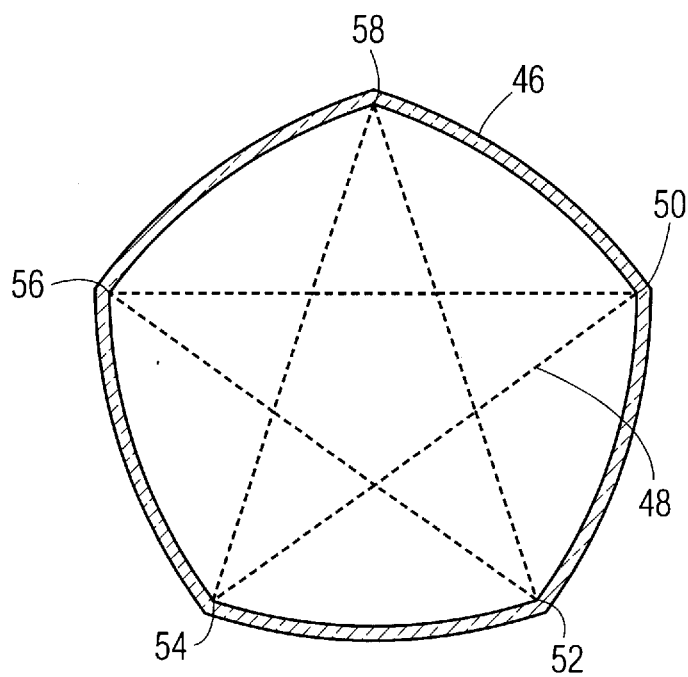
FIG. 4 shows a cross-section of a roller bottle (not shown), that describes substantially a pentagonal closed curve of constant width, for one embodiment of the invention.

FIG. 4 shows a cross-section 46 of a roller bottle (not shown), that describes substantially a pentagonal closed curve of constant width, for one embodiment of the invention. The shape is based on an imaginary pentagram 48. An imaginary pentagram 48 is constructed, the length of a leg of this pentagram 48 being the desired width. The point of a compass (not shown) is placed at 50 and a circular arc is drawn from opposing corner 54 to 56. The same procedure is repeated by placing the point of a compass at corner 52 and drawing an arc from corner 56 to 58, placing the point of a compass at corner 54 and drawing an arc from corner 58 to 50, placing the point of a compass at corner 56 and drawing an arc from corner 50 to 52, and again at corner 58 drawing an arc from corner 52 to 54. The connected arcs terminated at corners 50 and 52, 52 and 54, 54 and 56, 56 and 58 and 58 back to 50 describe a pentagonal closed curve of constant width that is the shape of a cross-section of a bottle of the invention.

Figure 5:
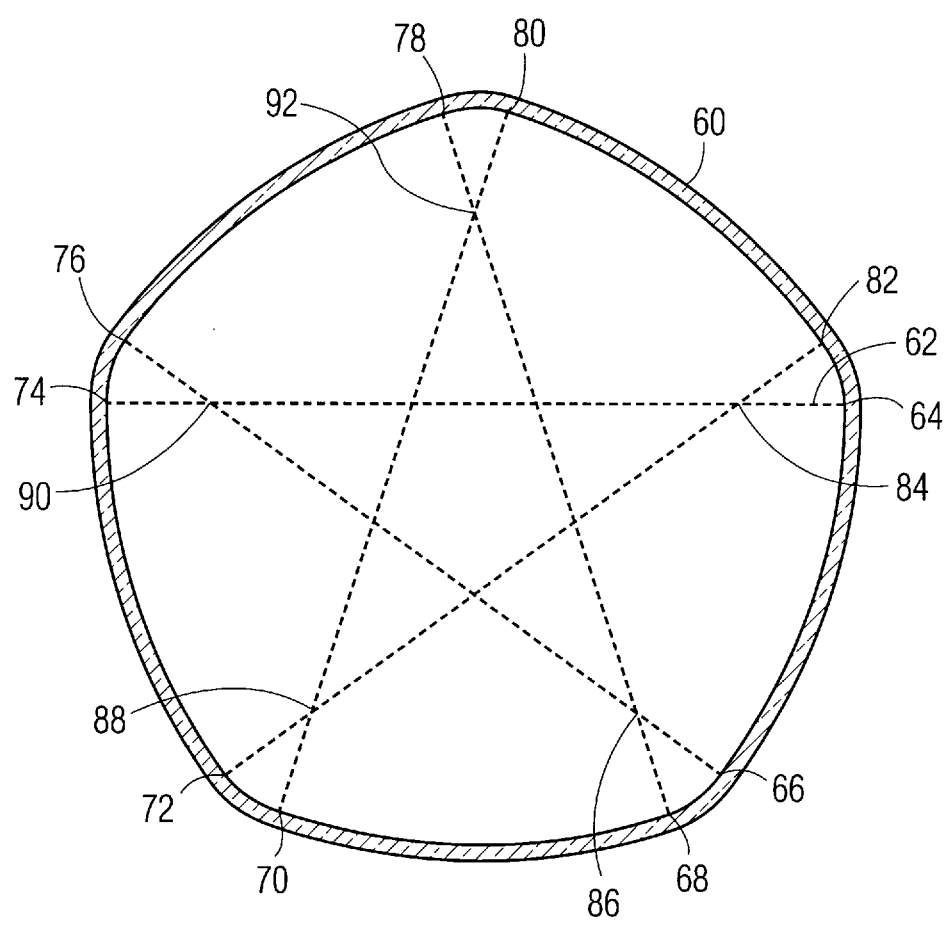
FIG. 5 shows a cross-section of a roller bottle (not shown), that describes substantially a pentagonal closed curve of constant width with rounded corners, for one embodiment of the invention.

FIG. 5 shows a cross-section 60 of a roller bottle (not shown), that describes substantially a pentagonal closed curve of constant width with rounded corners, for one embodiment of the invention. This shape may be constructed with an imaginary pentagram with extended legs 62. Place the point of a compass (not shown) at point 84 and draw an arc from points 64 to 82, with the point of a compass at the same location 84 draw opposing arc 72 to 74. Repeat this process with the point of a compass (not shown) at point 86 and draw an arc from points 66 to 68, with the point of a compass at the same location 86 draw opposing arc 76 to 78. Repeat this process with the point of a compass (not shown) at point 88 and draw an arc from points 70 to 72, with the point of a compass at the same location 88 draw opposing arc 80 to 82. Repeat this process with the point of a compass (not shown) at point 90 and draw an arc from points 74 to 76, with the point of a compass at the same location 90 draw opposing arc 64 to 66. Finally, repeat this process with the point of a compass (not shown) at point 92 and draw an arc from points 78 to 80, with the point of a compass at the same location 92 draw opposing arc 68 to 70. The joined arcs terminated at points 64 and 66, 66 and 68, 68 and 70, 70 and 72, 72 and 74, 74 and 76, 76 and 78, 78 and 80, 80 and 82 and 82 back to 64 describe a cross-section that is a pentagonal closed curved of constant width with rounded corners, having a width equal to one of the extended legs, such as that connecting points 70 and 80.

Although various embodiments of the invention are shown and described herein, they are not meant to be limiting, for example, those of skill in the art may recognize certain modifications to these embodiments, which modifications are meant to be covered by the spirit and scope of the appended claims. For example, the benefits of the invention accrue no matter what the material of construction or surface treatment and the invention may be used in combination with ribbing, hollow annulus shapes, pleats, inserts, packing material, automated apparatus, various caps, serrated rims, multiple interior surfaces, neutron bombardment of the walls to create gas permeable perforations and the like.

I claim:

1. In a process comprising a step for culturing cells in a roller bottle wherein the improvement comprises culturing said cells in a roller bottle comprising a cross-section that is substantially a non-circular closed curve of constant width.

2. A roller bottle comprising a cross-section that is substantially a non-circular closed curve of constant width, wherein the non-circular closed curve of constant width is substantially pentagonal.

3. The roller bottle of claim 2, wherein the non-circular closed curve of constant width is substantially pentagonal with rounded corners.

* * * * *